United States Patent [19]

Mayes et al.

[11] Patent Number: 4,741,814

[45] Date of Patent: May 3, 1988

[54] CONTAINER FOR AN ELECTROPHORETIC SUPPORT MEDIUM

[75] Inventors: David G. Mayes, Beaumont; James R. M. Sanford, Vidor; Eric H. Petersen, Beaumont, all of Tex.

[73] Assignee: Helena Laboratories Corporation, Beaumont, Tex.

[21] Appl. No.: 14,419

[22] Filed: Feb. 12, 1987

[51] Int. Cl.$^4$ .................. G01N 27/26; B65D 85/30; B65D 6/00

[52] U.S. Cl. .............. 204/299 R; 204/182.8; 206/454; 220/8; 220/356

[58] Field of Search ............ 204/299 R, 182.8; 220/8, 352, 356; 206/454, 455, 456

[56] References Cited

U.S. PATENT DOCUMENTS

| | | | |
|---|---|---|---|
| 3,379,303 | 4/1968 | Jenkins | 206/456 X |
| 3,463,301 | 8/1969 | Speelman | 206/456 |
| 4,314,897 | 2/1982 | Monte et al. | 204/299 R |

Primary Examiner—John F. Niebling
Assistant Examiner—John S. Starsiak, Jr.
Attorney, Agent, or Firm—Cullen, Sloman, Cantor, Grauer, Scott & Rutherford

[57] ABSTRACT

A container for protecting and enclosing an electrophoretic support medium is disclosed. The container includes a first portion and a second portion slidingly engageable with one another, whereby when closed they sealingly engage one another to form a substantially air-tight cavity therein. The first portion has a first recess defined by a protruding rim for accommodating a portion of the support medium therein. The second portion has a second recess defined by a protruding rim for accommodating the remainder of the support medium therein. The protruding rims are spaced apart from the bottoms of each portion and engagable with the base sheet of the support medium, whereby the support medium is retained within the recesses between the rims and the bottoms. The bottoms each have a substantially smooth planar surface to facilitate secure retention of the support medium.

7 Claims, 1 Drawing Sheet

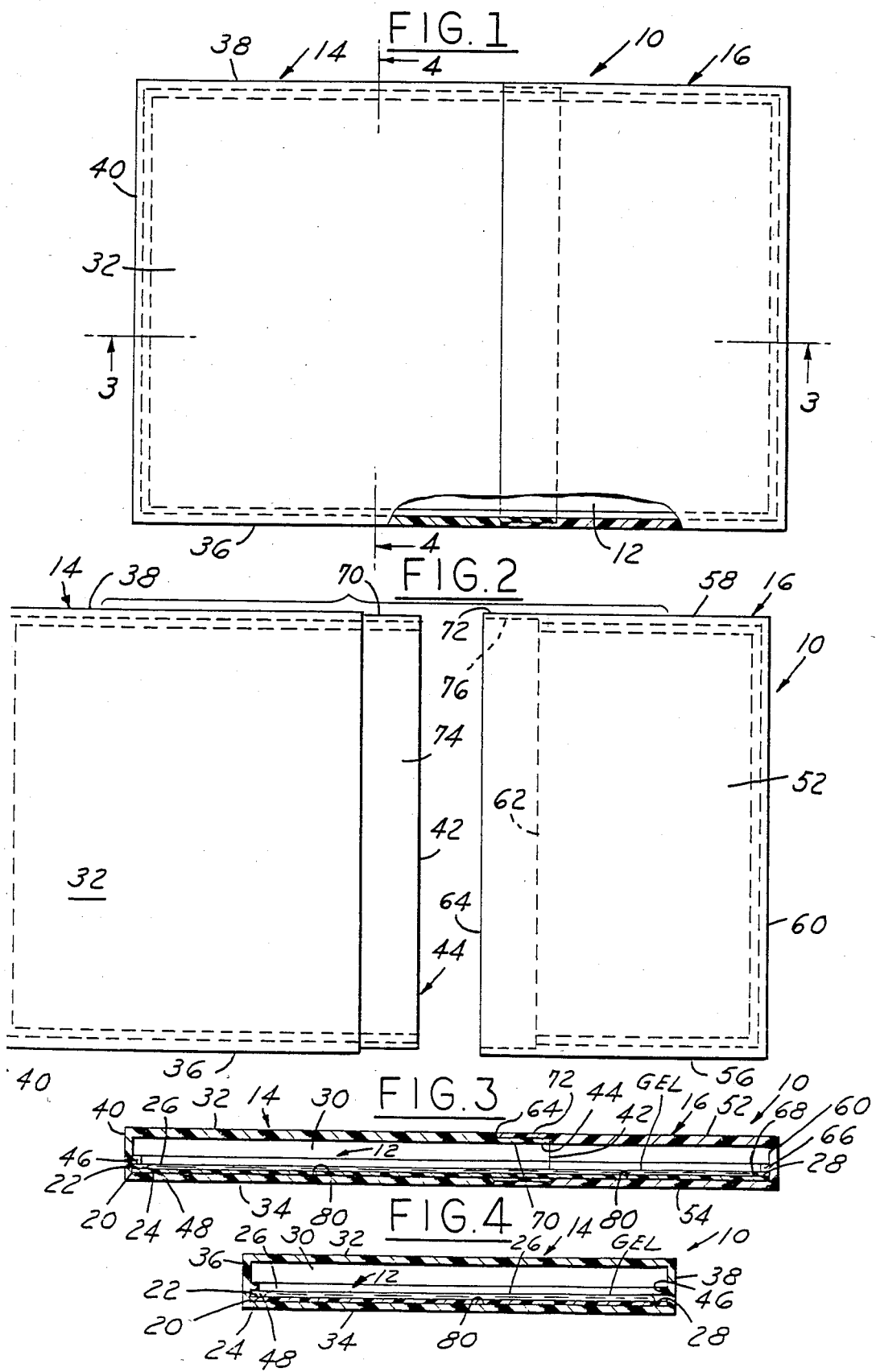

CONTAINER FOR AN ELECTROPHORETIC SUPPORT MEDIUM

FIELD OF THE INVENTION

The present invention relates generally to electrophoresis and particularly to a container for storing and protecting an electrophoretic support medium therein.

BACKGROUND OF THE INVENTION

It is known that an analysis of ionizable compounds, such as proteins, can be made by subjecting a sample, of for example blood, to an electrical potential as taught in U.S. Pat. Nos. 3,407,133 (Oliva et al.), 3,479,265 (Elevitch) and 3,875,045 (Bergrahm et al.). The sample to be analyzed by electrophoresis is placed on a suitable support medium, such as a gel, of the types disclosed in U.S. Pat. No. 3,725,004 (Johnson et al.). Such support medium may include, for example: (1) aqueous solutions of agar or agarose as disclosed in U.S. Pat. Nos. 3,281,409 (Blethen), 3,335,127 (Polson), 3,362,884 (Morse) and 3,766,047 (Elevitch); (2) synthetic polymeric gelling agents as disclosed in U.S. Pat. No. 3,046,201 (White et al.); and (3) cellulose and cellulose acetate as disclosed in U.S. Pat. No. 3,360,440 (Haab et al.). However, such containers require secure retention of the electrophoretic support medium within the container to prevent the support medium from coming in contact with any part of the container to prevent flaws, such as marks or cracks, from being formed in the support medium. Such flaws are aggravated by shrinkage of the support medium caused by dehydration as disclosed, for example, in U.S. Pat. No. 4,314,897 (Monte et al.).

SUMMARY OF THE INVENTION

In contrast to the prior art containers for storing and protecting an electrophoretic support medium from physical damage and dehydration acknowledged above, the container of the present invention provides a means for securely retaining the support medium within the container whereby the support medium may be inserted into the container between a rim and the bottom of the container to be retained therein when the container is closed.

The container of the present invention, for protecting and enclosing an electrophoretic support medium having a base sheet with at least two opposed major surfaces and a layer of an electrophoretic gel adhered to one of the major surfaces of the base sheet, includes a first portion and a second portion. The first portion has a top, a bottom and a plurality of sides joining the top and the bottom and a side which is open. Similarly, the second portion has a top, a bottom and a plurality of sides joining the top and the bottom and a side which is open. The first portion and the second portion when closed are sealingly engagable with one another along the open sides to form a cavity therein. A first rim protrudes from at least one of the sides of the first portion into the cavity and is spaced apart from the bottom of the first portion to define a first recess. A second rim protrudes from at least one of the sides of the second portion into the cavity and is spaced apart from the bottom of the second portion to define a second recess. The first rim and the second rim are engageable with the base sheet of the electrophoretic support medium so that when the electrophoretic support medium is placed in the recesses between the rims and the bottoms of the portions when the container is closed, the electrophoretic support medium may be retained therein.

In the preferred embodiment, the rims protrude into the cavity from the sides of the portions to form a continuous rim about the sides joining the tops and the bottoms when the container is closed.

Also, in the disclosed embodiment, the first portion may include an inner lip and the second portion may include an outer lip about their open ends. The lips each include a continuous sealing surface, whereby, when the container is closed, the inner lip extends into the outer lip so that the continuous sealing surfaces engage one another to seal the container to form a substantially air-tight cavity.

In a further embodiment, the rims are spaced apart from the bottoms sufficiently so that the base sheet of the electrophoretic support medium may be placed between the rims and the bottoms to prevent contact with the gel layer.

BRIEF DESCRIPTION OF THE DRAWINGS

The various features, benefits, and advantages of the present invention will become more apparent by reading the following detailed description in conjunction with the drawings where like reference numerals identify corresponding components, and:

FIG. 1 is a plan view of the container of the present invention, partially in fragmentary, illustrating the container in an closed position with the electrophoretic support medium retained therein;

FIG. 2 is a plan view of the container with the container in an opened position illustrating the details of the first portion and the second portion;

FIG. 3 is a side view of the container, in section, illustrating the details of the container in the closed position and the details of the electrophoretic support medium with the layer of electrophoretic gel adhered to the base sheet taken in the direction of arrows 3—3 of FIG. 1; and FIG. 4 is a side view of the container, in section, illustrating retention of the electrophoretic support medium therein by the protruding rim similar to FIG. 3 but taken from a different side in the direction of arrows 4—4 of FIG. 1.

DETAILED DESCRIPTION OF THE PREFERRED EMBODIMENT

Referring to FIG. 1 of the drawings, the container of the present invention, generally designated 10, for protecting and enclosing an electrophoretic support medium 12 is illustrated. The container 10, as best illustrated in FIG. 2, includes a first housing portion 14 and a second housing portion 16, which when closed sealingly engage with one another. The first portion 14 and the second portion 16 are slidingly engagable with one another to permit ease of opening and closing.

As illustrated in FIG. 1 and in greater detail in FIG. 3, the electrophoretic support medium 12 includes a base sheet 20 which has at least two opposed major surfaces 22 and 24. A layer 26 of an electrophoretic gel is adhered to one of the major surfaces 22 of the base sheet. In the preferred embodiment, the gel layer 26 is spaced apart from the peripheral edge 28 of the base sheet 20 so as to prevent contact of the gel layer with the container. The particular gel is not essential to the present invention and may include any of the mediums of the prior art mentioned hereinabove. However, agarose has been successfully utilized.

When the container 10 is closed by slidingly engaging the housing portions 14 and 16, a cavity 30 is formed within the container by the first portion 14 and the second portion 16, as illustrated in FIGS. 3 and 4.

The first portion 14, in the preferred embodiment, includes a top 32 and a bottom 34 joined by two sides 36, 38, and end wall and 40. Two of the sides 36 and 38 are opposed sides and a fourth side or end, 42 is open to form an open end 44. A first rim 46 protrudes into the cavity 30 from the sides 36, 38 end wall and 40, joining the top and bottom, to form a first recess 48 defined by the rim 46 and the bottom 34 of the first portion 14. The first rim 46 is spaced apart from the bottom 34 a sufficient distance so that the base sheet 20 is engagable therewith and may fit therebetween in the recess 48. Also, the first rim 46 protrudes into the cavity only a predetermined distance to cooperate with the amount the gel layer 26 is spaced apart from the peripheral edge 28 of the base sheet 20 so as not to come in contact with the gel layer 26.

Likewise the second housing portion 16 includes a top 52 and a bottom 54 joined by two sides 56, 58, and and end wall 60. Two of the sides 56 and 58 are opposed sides and a fourth side or end 62 is open to form an open end 64. A second rim 66 protrudes into the cavity 30 from the sides 56, 58 and end wall 60, and is similarly spaced apart from the bottom 54 to form a second recess 68.

In the preferred embodiment, the first rim 46 and second rim 66 protrude from all of the sides and end walls 36, 38, 40, 56, 58 and 60 to form a continuous rim when the first portion 14 and the second portion 16 are slid together to close the container 10. Thus, to close the container, either housing portion 14 or 16 is first slid over a portion of the electrophoretic support medium 12 in the recess and then the other portion is slid over the remainder of the electrophoretic support medium 12 extending from the initial portion into the recess. In addition, the rims 46 and 66 are spaced apart from their respective tops 32 and 52 to form spaces or additional recesses above the electrophoretic support medium 12 to insure that the tops do not come in contact with the gel layer 26. It should be appreciated that a discontinuous rim formed by, for example, a plurality of nubs or the like may protrude from the sides into the cavity without departing from the present invention. However, a continuous rim is preferred to facilitate insertion of the electrophoretic support medium 12 into the recesses 48 and 68, and to facilitate manufacture of the container 10.

To close the container, the first housing portion 14 is provided with an inner annular lip 70 about its open end 44, and the second portion is provided with an outer lip 72 about its open end 64, which are slidingly engagable with one another. To provide a substantially air-tight cavity, the inner lip 70 includes a continuous sealing surface 74 and the outer lip 72 includes a continuous sealing surface 76, which come in contact with one another to seal the open ends 44 and 64 of the portions 14 and 16 when the container 10 is closed.

At least a portion of the bottom 34 of the first recess 48 and the bottom 54 of the second recess 68 may include a substantially smooth planar surface 80. The surfaces should be substantially smooth to maximize contact between the other or exposed surface 24 of the base sheet 20 and the planar surfaces 80 of the recesses 48 and 68 to facilitate secure retention of the support medium 12. This will assist in retaining the electrophoretic support medium 12 within the cavity 30 through air situated between the base sheet 20 and the bottoms 34 and 54 of the recesses 48 and 68, or through a liquid situated between the base sheet 20 and the bottoms 34 and 54, thus using the "molecular attractions" of surface tension and capillary attraction.

The particular materials of which the container 10 and base sheet 20 are made is not essential to the present invention. However, it has been found that polymeric materials, such as styrene for the container and Mylar for the base sheet ("MYLAR" is a trademark of E. I. DuPont de Nemours & Company of Wilmington, Del.), are satisfactory. Normally, a manufacturer of this product will select the best commercially available material based upon price, application and manufacturing process.

There are several ways to produce the container 10 of the present invention which are known to those skilled in the art, such as vacuum forming or injection molding. The particular manufacturing process is not essential to the present invention, and is a matter of choice based upon economics and availability.

While the preferred embodiment of the present invention has been described so as to enable one skilled in the art to practice the present invention, the proceeding description is intended to be exemplary and should not be used to limit the scope of the invention. The scope of the invention should be determined only by reference to the following claims.

We claim:

1. A container for protecting and enclosing an electrophoretic support medium having a base sheet with at least two opposed major surfaces and a layer of an electrophoretic gel adhered to one of the major surfaces of the base sheet, said container comprising:

a pair of separable first and second housing portions, each housing portion having a pair of ends, a top, a bottom, a pair of side walls and an end wall at one of the ends joining said top, bottom and side walls, the other end of each housing portion forming an entrance to the interior of the housing portion;

said other end of one of said housing portions being provided with an inner annular lip and the other end of said other housing portion being provided with an outer annular lip;

said inner annular lip of said one housing portion slidably extending into the outer annular lip of the other housing portion when the housing portions are assembled to form a cavity therein;

an internal first rim protruding from the side walls and said one end wall of said first housing portion and said inner annular lip into said cavity, and first rim being spaced apart from the bottom of said first portion to define a first recess in said cavity;

an internal second rim protuding from the side walls and said one end wall of said second housing portion into said cavity, said second rim being spaced apart from the bottom of said second portion to define a second recess in said cavity;

said first and second rims being spaced from the bottoms the same distance;

the recess of one of said housing portions adapted to receive part of the electrophoretic support medium inserted through the entrance thereof, with the corresponding rim being engageable solely with the base sheet of the support medium; and the recess of the other of the housing portions adapted to receive the remaining part of the electrophoretic support medium inserted through the entrance thereof, with the corresponding rim also being engageable solely with the base sheet of the support medium;

said housing portions when assembled having the inner annular lip in sealing engagement with said outer annular lip and with the end surfaces of said first rim on said inner annular lip abutting the end surfaces of the opposing second rim.

2. The container defined in claim 1, wherein the bottom of said first housing portion further comprises a substantially smooth planar surface.

3. The container defined in claim 2, wherein the bottom of said second housing portion further comprises a substantially smooth planar surface.

4. The container defined in claim 1, wherein said first rim is spaced apart from the top of said first housing portion to prevent contact with the portion of said electrophoretic support medium located in said first recess when said container is closed.

5. The container defined in claim 4, wherein said second rim is spaced apart from the top of said second housing portion to present contact with the portion of said electrophoretic support medium located in said second recess when said container is closed.

6. The container defined in claim 1, wherein said container is made of a polymeric material.

7. The container defined in claim 6, wherein the polymeric material is styrene.

* * * * *